United States Patent
Gur et al.

(10) Patent No.: US 11,200,975 B2
(45) Date of Patent: Dec. 14, 2021

(54) FRAMEWORK FOR MODELING COLLECTIONS AND THEIR MANAGEMENT

(71) Applicant: INTERNATIONAL BUSINESS MACHINES CORPORATION, Armonk, NY (US)

(72) Inventors: Yaniv Gur, San Jose, CA (US); Tanveer F. Syeda-Mahmood, Cupertino, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 96 days.

(21) Appl. No.: 16/181,500

(22) Filed: Nov. 6, 2018

(65) Prior Publication Data

US 2020/0143933 A1    May 7, 2020

(51) Int. Cl.
*G06F 17/00* (2019.01)
*G16H 30/20* (2018.01)
*G06F 16/51* (2019.01)

(52) U.S. Cl.
CPC .............. *G16H 30/20* (2018.01); *G06F 16/51* (2019.01)

(58) Field of Classification Search
CPC ........ G16H 30/20; G16H 40/20; G16H 10/60; G06F 16/51; G06F 16/13; G06F 16/134; G06F 16/14; G06F 16/182; G06F 16/1858; G06F 16/1865; G06F 16/1873; G06F 16/2264; G06F 16/2308

See application file for complete search history.

(56) References Cited

U.S. PATENT DOCUMENTS

| | | | |
|---|---|---|---|
| 6,408,330 B1* | 6/2002 | DeLaHuerga | A61J 7/0084 709/217 |
| 6,466,933 B1* | 10/2002 | Huang | G06F 16/256 707/759 |
| 9,223,482 B2* | 12/2015 | Schulze | G06F 3/0486 |
| 10,963,821 B2* | 3/2021 | Barnes | G16H 80/00 |
| 2005/0246205 A1* | 11/2005 | Wang | G16H 10/60 705/3 |
| 2007/0217665 A1 | 9/2007 | Kiraly et al. | |
| 2008/0021918 A1* | 1/2008 | Rao | G06F 16/958 |
| 2008/0212861 A1 | 9/2008 | Durgan et al. | |
| 2014/0365243 A1* | 12/2014 | Varadan | G16H 10/60 705/3 |

(Continued)

OTHER PUBLICATIONS

F. Lu and X. Li, "RCBA: An Efficient Annotation Tool for Community E-Learning," 2011 Fifth International Conference on Genetic and Evolutionary Computing, Xiamen, pp. 353-356, doi: 10.1109/ICGEC.2011.88, Sep. 2011.*

(Continued)

*Primary Examiner* — Greta L Robinson
(74) *Attorney, Agent, or Firm* — Erik Huestis; Stephen Kenny; Foley Hoag LLP

(57) ABSTRACT

Management of collections of medical documents is provided. In various embodiments, search criteria are specified for one or more datastore. Location information for a plurality of medical documents (e.g. images, textual documents, time series data, etc.) is retrieved from the one or more datastore. The location information for the plurality of medical documents is aggregated into a virtual collection. The virtual collection is indexed by metadata of the virtual collection.

19 Claims, 5 Drawing Sheets

(56) References Cited

U.S. PATENT DOCUMENTS

2016/0170814 A1\* 6/2016 Li .................. G06Q 10/10
719/318
2016/0232658 A1 8/2016 Syeda-Mahmood
2019/0147588 A1\* 5/2019 Rowley Grant ....... G16H 30/40
382/131

OTHER PUBLICATIONS

T.V. Krishnamurthy, Sapna Subramani, Ailments of Distributed Document Reviews and Remedies of DOCTOR (DOCument Tree ORganizer Tool) with Distributed Reviews Support, 2008 International Conference on Global Software Engineering, pp. 210-214, DOI: 10.1109/ICGSE.2008.8, Oct. 3, 2008.\*

\* cited by examiner

FRAMEWORK FOR MODELING COLLECTIONS AND THEIR MANAGEMENT

BACKGROUND

Embodiments of the present disclosure relate to medical imaging studies, and more specifically, to management of collections of medical documents.

BRIEF SUMMARY

According to embodiments of the present disclosure, methods of and computer program products for medical image collection management are provided. In various embodiments, search criteria are specified for one or more datastore. Location information for a plurality of medical documents (e.g. images) is retrieved from the one or more datastore. The location information for the plurality of medical images is aggregated into a virtual collection. The virtual collection is indexed by metadata of the virtual collection.

DETAILED DESCRIPTION

Figure 1:
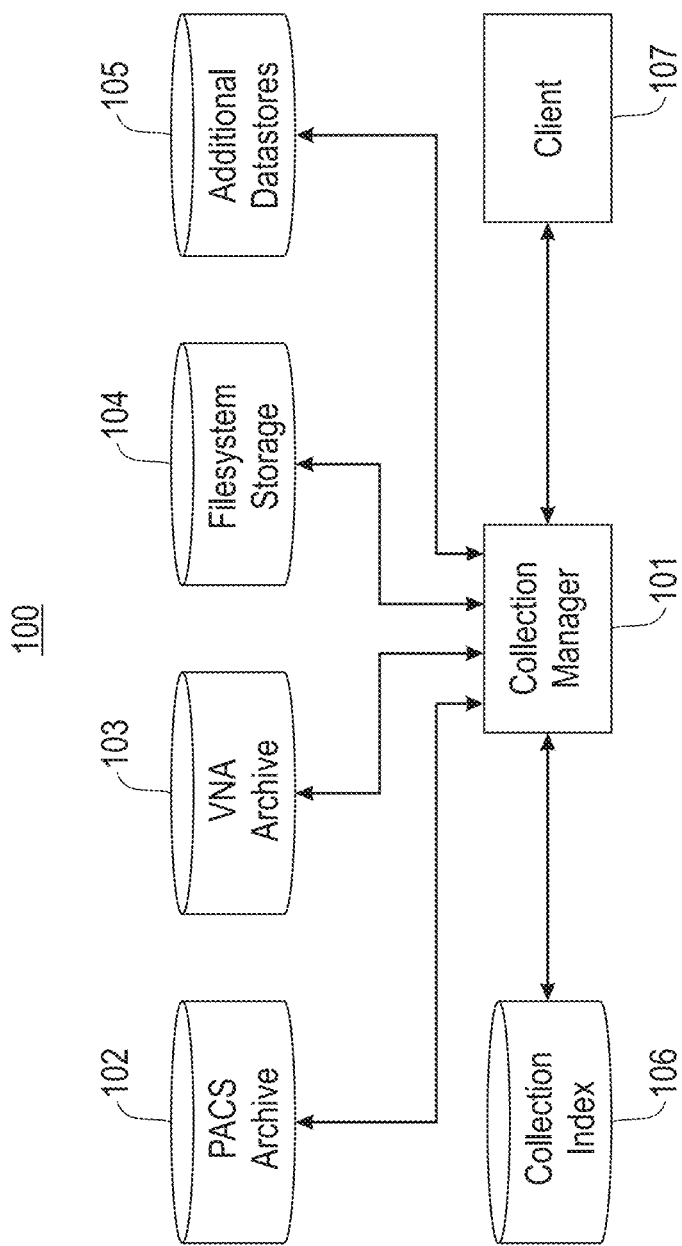
FIG. 1 illustrates a system for medical image collection management according to embodiments of the present disclosure.

As deployment of image analytics becomes widespread, there is a need for a common platform to organize collections of medical imagery, organize the annotation of those collections, and organize the running of analytics on those collections. Such a platform is particularly useful for organize testing and benchmarking efforts to enable continuous improvement of algorithms. Such a platform may be deployed as a hosted service.

The present disclosure addresses the creation and handing of collections of medical documents (e.g., text reports, images, time series data, etc.) from multiple underlying sources. Aggregate collections, or virtual collections, provide a data model for logical organization of underlying repository data. These virtual collections are persisted with various metadata for searching and later retrieval. Virtual collections backed by disparate underlying datastores allow a user to assemble, organize, and edit collections without modifying the organization of the underlying data. In addition, virtual collections may be searched according to their metadata, thereby allowing a user to leverage prior collection assembly work and increasing reproducibility of aggregate studies.

Aggregate or virtual collections may be formed at an arbitrary resolution. For example, irrespective of the number of backing datastores, a virtual collection may cover an organization, a patient, a study, an exam, a run or sequence, an image, a patch, or pixels. It will be appreciated that collections may be assembled at multiple resolutions, or across multiple of these categories, for example providing all CT slices depicting a coronary artery for a given hospital. Class labels may be assigned to a given collection for future retrieval and analysis.

As noted above, a variety of underlying datastores are suitable for according to the present disclosure. For example, all images within an underlying datastore may be maintained as files within a directory of a filesystem. In some embodiments, the images may be stored as raw image files. In such embodiments, a file listing of the relevant directory would yield a listing of all relevant images. Various interfaces may be available to interact with the underlying datastore, such as standard file transfer techniques, such as FTP, WebDAV, or various local or network-accessible file systems and transfer protocols.

In another example, an underlying datastore may include a VNA or PACS systems. Data may be automatically ingested from a PACS or VNA system using existing interfaces to such systems, including for searching and browsing within a VNA or PACS system.

A Vendor Neutral Archive (VNA) is a medical imaging technology in which images and documents (and potentially any file of clinical relevance) are stored (archived) in a standard format with a standard interface, such that they can be accessed in a vendor-neutral manner by other systems.

A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM. Communication with a PACS server, may be done through DICOM messages that that contain attributes tailored to each request. For example, once a client initiates a connection, it can prepare a DICOM message, which may be a C-FIND, C-MOVE, C-GET, or C-STORE request. The client fills in the DICOM message with the keys that should be matched, allowing search and retrieval of data from a PACS system.

With reference now to FIG. 1, a system for medical image collection management is illustrated according to embodiments of the present disclosure. Collection Manager 101 has access to datastores 102 . . . 105 containing underlying data. As noted above, a variety of underlying datastores may be used as set out herein, including PACS archives 102, VNA Archives 103, Filesystem storage 104, or Additional Datastores 105. Some datastores provide datastore-specific search and access methods. For example, PACS Archive 102 may be accessed via DICOM message. Filesystem Storage 104 may be accessed by WebDAV or various other local or network-accessible file systems.

Collection Manager 101 creates virtual collections containing one or more sample, image, or other data element from one or more underlying datastore 102 . . . 105. Each virtual collection is associated with metadata regarding the collection, for example a name, label, source, comments, size, etc. Each virtual collection also includes location information for each data element. For example, location information may include a URL, unique record identifier, file path, or search string that is applicable to one of the underlying datastores 102 . . . 105 to access the underlying data.

Each virtual collection is stored and indexed in Collection Index 106. In some embodiments, the collection index is based on a directory structure in a file system. In some such embodiments, metadata files are stored in or alongside directories corresponding to individual collections. Metadata files may provide information about each collection, including associated patient data, or collection descriptions. In some such embodiments, data samples are linked to from the index as noted above. However, in some embodiments a combined datastore and index may be provided, in which data elements may be located within the directory structure of the collection index.

In some embodiments, the Collection Index 106 is indexed using Apache Lucene, although it will be appreciated that a variety of indexing and searching tools may be used for this purpose.

In some embodiments, Collection Index 106 comprises a relational database. In such embodiments, collections are stored and indexed within one or more database tables.

In some embodiments, Collection Manager 101 is used to assign annotators and annotation tasks. For example, Collection Manager 101 may be integrated into a platform for creation and organization of image collections from large image repositories for the purpose of training and testing image analytics algorithms and products. Collections are assigned to registered clinical experts for annotation. These annotations serve as ground truth for training and testing of analytics. Various browser-based tools are provided for annotation of medical images, and various data structures are provided that support search and retrieval of collections and annotations. The running of analytics on collections and the generation of performance reports may be organized through the same user interface.

More generally, Collection Manager 101 may provide a client interface 107 that may be used by external tools to provide collection generation of medical data collections, collection annotation of medical data such as imagery in the various collections under management, and analytic runs against the medical data such as imagery in the various collections under management.

Once collections of underlying medical data are formed, information regarding those collections may be stored in Collection Index 106. Various machine learning (ML) algorithms may be applied to the stored collection. The present disclosure provides common platform to organize collections, organize annotation of collections, organize running of analytics on collections, organize testing and benchmarking efforts and enable continuous improvement of algorithms for productization. In various embodiments, this is provided as a hosted service.

In various embodiments, collections may be browsed through a user interface. In some embodiments, a hierarchical view of the collections is provided. In addition, in some embodiments, collections may be searched according to user-defined criteria. Images belonging to a collection may likewise be searched. Search results may be combined to form a new collection. For example, while data may originally be ingested from PACS organized by patient and study, a custom collection may be defined of all images from a certain study type having a given label (e.g., all echocardiograms labeled for stenosis). In some embodiments, the images resulting from a search are displayed to a user to be marked for inclusion in a collection.

In embodiments providing annotation, Collection Manager 101 may route user-provided annotations back to the underlying datastore to be maintained with the original medical data. Collection Manager 101 may also associate annotators with collections via the metadata in Collection Index 106.

In various embodiments, Collection Manager 101 exposes an API for search, retrieval, and modification of collections. For example, in some embodiments, Collection Manager 101 provides a REST API that is used by client 107.

Accordingly, systems of the present disclosure are adapted to access medical images from locally saved files, Vendor Neutral Architecture (VNA) repositories, Picture Archiving and Communications Systems (PACS) repositories, or images selected from a user search query. Systems according to the present disclosure may provide a user interface enabling hierarchical collection browsing, searching collections based on various input criteria, and searching medical images within a specified collection. Systems according to the present disclosure enable updating of collections, the user interface displaying at least one medical image having a collection identifier and allowing a user to associate images from a first collection with additional collections.

In some embodiments, a user interface is provided that allows a user to browse raw collections. In some embodiments, hierarchical collection browsing is provided.

In some embodiments, a user interface is provided that allows a user to search collections. In some embodiments, collection may be searched based on user-specific criteria. In some embodiments, a user may search images belonging to selected collections.

In some embodiments, additional collection may be created by combining the constituents of existing collections. In some embodiments, a user interface is provided that displays images and allows a user to mark those that should be included in collections.

In various embodiments, a user interface is provided that allows a user to update collections. In some embodiments, this includes the ability to add descriptions to individual collections. In some embodiments, a user may associate features of interest with collections.

In some embodiments, all raw images in a collection are stored in a filesystem as described herein, even when drawn from an underlying VNA or PACS. In some embodiments, fictitious patients are associated with collections to ensure confidentiality when using medical imagery for system training purposes. In some embodiments, cloud storage is used for the medical imagery. In some embodiments, a federated or a cooperative storage architecture may be used. In some embodiments, centralized storage of image files is provided. In some embodiments, storage mirrors are provided.

Figure 2:
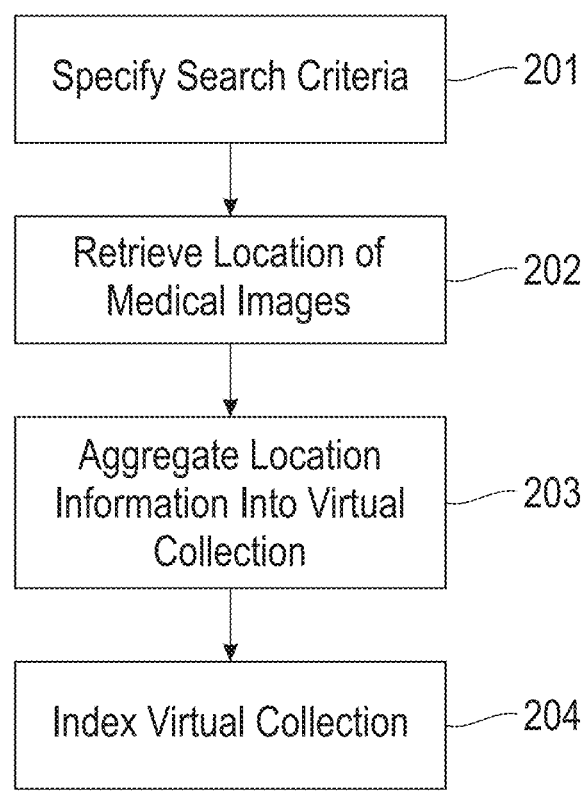
FIG. 2 illustrates a method for medical image collection management according to embodiments of the present disclosure.

With reference now to FIG. 2, a method for creating a virtual collection is illustrated according to embodiments of the present disclosure. At 201, search criteria are specified for one or more underlying datastore. The search criteria may indicate a whole study, or may span studies. At 202, data conforming to the search criteria are retrieved from a datastore. In some embodiments, a listing of the results is provided to a user for selection of the results to include in a new virtual collection. In some embodiments, all results from the search are included in a new collection. At 203, the virtual collection is specified. In some embodiments, the collection specification includes a name, type, task for which the collection is relevant, any metadata to describe the collection, and parent or child information for a nested collection. At 204, the collection is indexed.

Subsequent to collection creation, the collection may be located by searching in the collection index. Tasks, such as annotation tasks, may be associated with a given collection. A collection may be associated with a new task by creating a copy of the original virtual collection and associating a new task with that new copy.

Collections may be merged by merging the list of constituent data of several collections and creating a new virtual collection. In some embodiments, the new virtual collection may be flagged as the child of the source collections.

Figure 3:
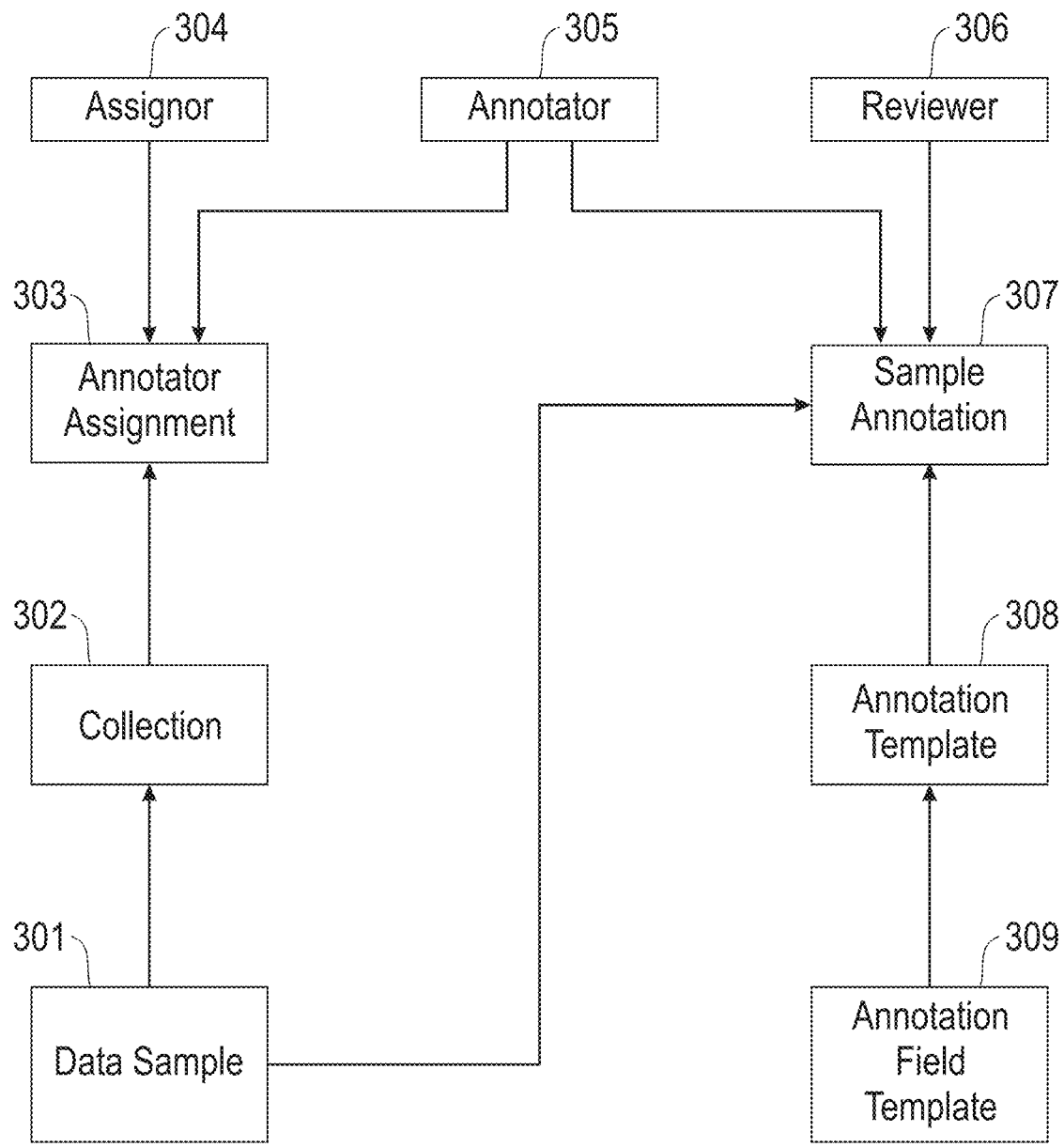
FIG. 3 illustrates an exemplary collection data model according to embodiments of the present disclosure.

Referring now to FIG. 3, an exemplary collection data model is depicted in which a data sample 301 (e.g. images, textual documents, time series data, etc.) is included in a collection 302 which can share a common logical connection. An annotator assignment 303 is included which communicates with the Assignor 204 and Annotator 305. The Annotator 305 enables annotations to be applied to the sample annotation 307 dataset, which can also be reviewed by Reviewer 306. Additionally, an annotation template 308, which can describe what annotation needs to be applied to a particular dataset, and annotation field template 309 can be applied to the sample annotation 307. This configuration is advantageous in that it can provide a common annotation to be applied across numerous documents, and/or provide a field type which designates what types of annotations are permissible at a particular location within the document. The Assignors 204 can provide access/privilege/assign annotators to a given data collection. In an exemplary embodiment, the annotations can represent a triplet of data-annotator-and-annotation templates. Also, the Reviewer 306 is a peer (relative to the Annotator 405 and/or Assignor 406) who reviews the given collection. Accordingly, the data model of the present disclosure provides a framework which allows for machine learning of any kind to be completed on any kind of data.

Figure 4:
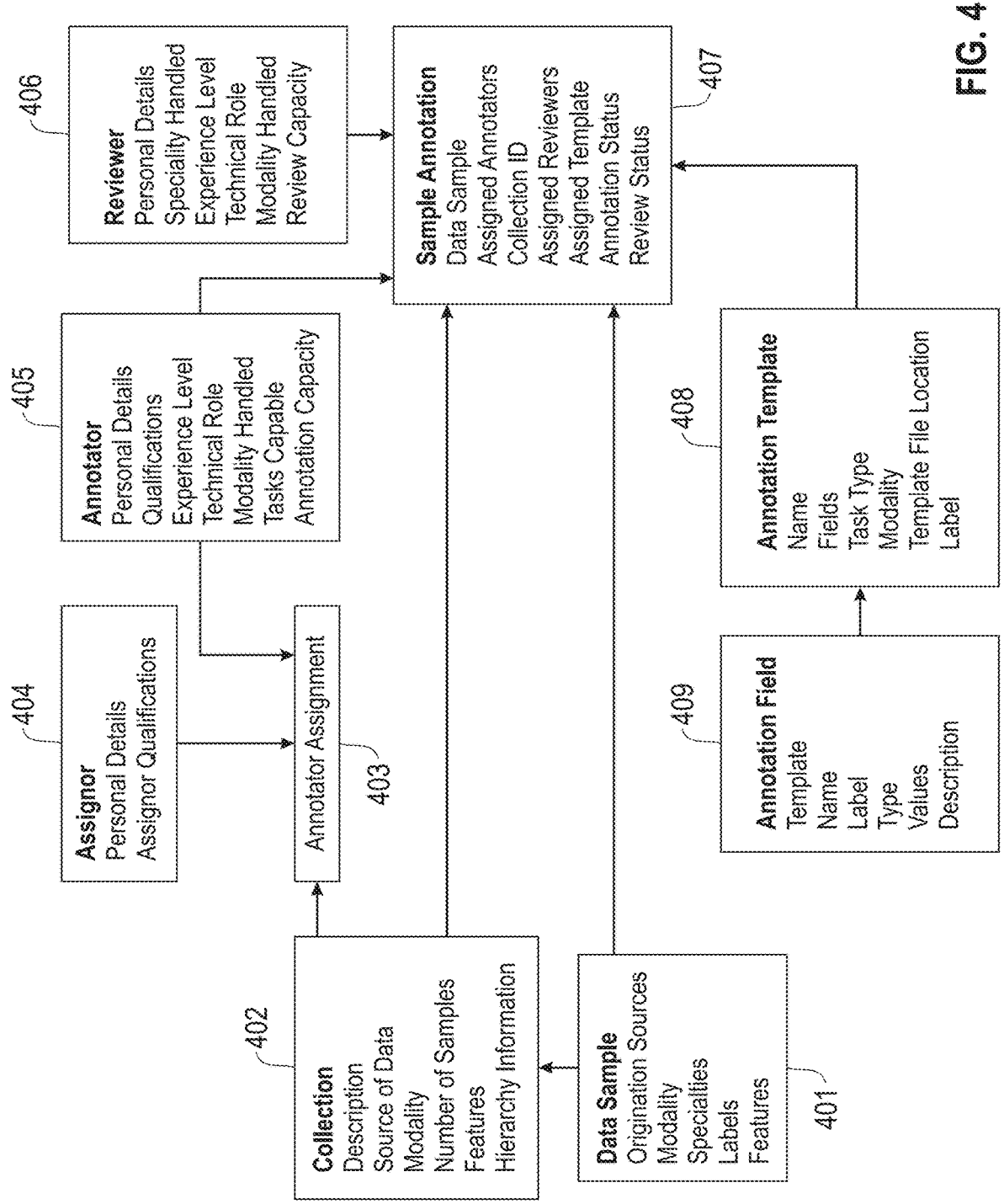
FIG. 4 illustrates an exemplary information model according to embodiments of the present disclosure.

Referring now to FIG. 4, an exemplary information model is depicted in which lists, for purpose of illustration and not limitation, typical types of information which can be incorporated within the scope of the present disclosure.

Figure 5:
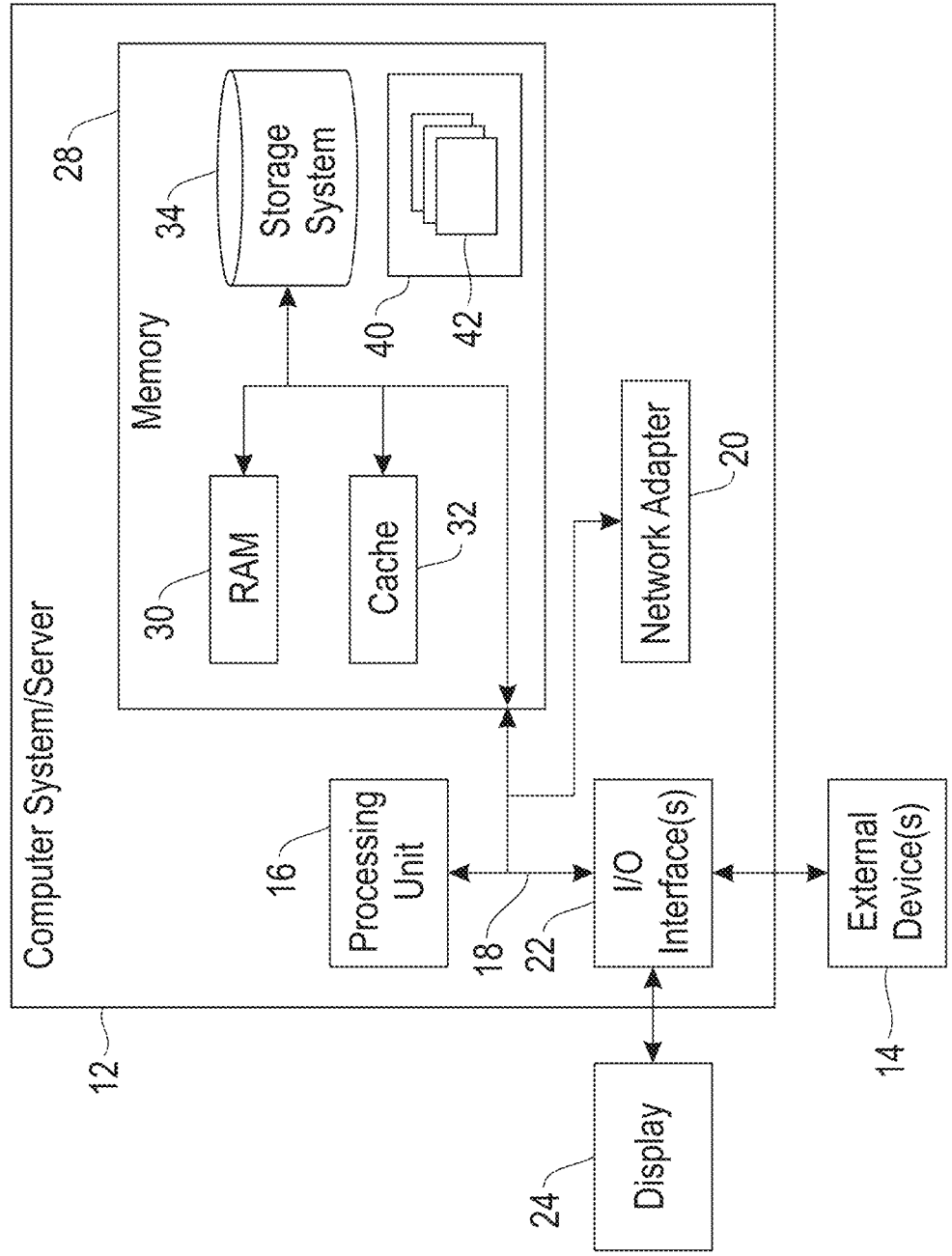
FIG. 5 depicts a computing node according to an embodiment of the present invention.

Referring now to FIG. 5, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
specifying search criteria for a plurality of datastores;
retrieving, from the plurality of datastores, location information for each medical document of a plurality of medical documents, wherein the location information for each medical document comprises a uniform resource locator (URL), a unique record identifier, a file path, or a search string applicable to one of the plurality of datastores;
aggregating the location information for the plurality of medical documents into a virtual collection stored at a virtual collection server, the virtual collection relating to a patient, a study, or an exam and the location information being applicable to access each of the plurality of medical documents from the plurality of datastores;
indexing the virtual collection by metadata of the virtual collection;
storing the indexed virtual collection at a collection index;
accessing an annotation template, the annotation template identifying at least one annotation type for the virtual collection; and
providing the virtual collection to a user for annotation based on the annotation template.

2. The method of claim 1, wherein the plurality of medical documents comprises an image.

3. The method of claim 1, wherein the plurality of medical documents comprises a textual document.

4. The method of claim 1, wherein the search criteria specify a complete medical document study.

5. The method of claim 1, wherein the search criteria specify medical documents from multiple medical document studies.

6. The method of claim 5, wherein the directory structure reflects the hierarchy of the virtual collection.

7. The method of claim 1, wherein the metadata of the virtual collection includes name, label, source, comments, or size.

8. The method of claim 1, further comprising:
receiving an annotation from the user;
routing the annotation to one of the plurality of datastores.

9. The method of claim 8, further comprising:
presenting the annotation to a peer for review.

10. The method of claim 1, further comprising:
receiving a search query from a user;
providing the virtual collection in response to the search query.

11. The method of claim 1, further comprising:
generating a second virtual collection from the virtual collection.

12. The method of claim 1, wherein each of the plurality of datastores comprises a file system, a Vendor Neutral Architecture (VNA), or a Picture Archiving and Communications System (PACS).

13. The method of claim 1, wherein the virtual collection is represented by a node in a directory structure.

14. The method of claim 1, wherein the user interface is a web interface.

15. A system comprising:
a computing node comprising a computer readable storage medium having program instructions embodied therewith, the program instructions executable by a processor of the computing node to cause the processor to perform a method comprising:
specifying search criteria for a plurality of datastores;
retrieving from the plurality of datastores location information for each medical document of a plurality of medical documents, wherein the location information for each medical document comprises a uniform resource locator (URL), a unique record identifier, a file path, or a search string applicable to one of the plurality of datastores;
aggregating the location information for the plurality of medical documents into a virtual collection stored at a virtual collection server, the virtual collection relating to a patient, a study, or an exam and the location information being applicable to access each of the plurality of medical documents from the plurality of datastores;
indexing the virtual collection by metadata of the virtual collection;
storing the indexed virtual collection at a collection index;
accessing an annotation template, the annotation template identifying at least one annotation type for the virtual collection; and
providing the virtual collection to a user for annotation based on the annotation template.

16. The system of claim 15, wherein the medical documents is an image.

17. The system of claim 15, wherein the annotation is presented to a peer for review.

18. A computer program product for medical document collection management, the computer program product comprising a computer readable storage medium having program instructions embodied therewith, the program instructions executable by a processor to cause the processor to perform a method comprising:
specifying search criteria for a plurality of datastores;
retrieving from the plurality of datastores location information for each medical documents of a plurality of medical documents, wherein the location information for each medical document comprises a uniform resource locator (URL), a unique record identifier, a file path, or a search string applicable to one of the plurality of datastores;
aggregating the location information for the plurality of medical documents into a virtual collection stored at a virtual collection server, the virtual collection relating to a patient, a study, or an exam and the location information being applicable to access each of the plurality of medical documents from the plurality of datastores;
indexing the virtual collection by metadata of the virtual collection;
storing the indexed virtual collection at a collection index;

accessing an annotation template, the annotation template identifying at least one annotation type for the virtual collection; and providing the virtual collection to a user for annotation based on the annotation template.

19. The computer program product of claim 18, wherein the medical documents is an image.

\* \* \* \* \*